United States Patent [19]

Yoshida

[11] Patent Number: Plant 5,292

[45] Date of Patent: Oct. 9, 1984

[54] AFRICAN VIOLET

[76] Inventor: Eiichi Yoshida, P.O. Box 4836, Hayward, Calif. 94540

[21] Appl. No.: 473,623

[22] Filed: Mar. 9, 1983

[51] Int. Cl.[3] ..... A01H 5/00

[52] U.S. Cl. ..... Plt./69

[58] Field of Search ..... Plt./69

*Primary Examiner*—Robert E. Bagwill

[57] ABSTRACT

A new variety of African violet plant for potted plant culture particularly distinguished by its year around blooming capability, its profuse production of dark violet and white, pansy-like flowers, and its compact growth with abundant foliage of solid green color on the upper side which provide a spreading base and attractive backing for the clusters of blossoms.

1 Drawing Figure

BACKGROUND OF THE NEW PLANT

This new variety of African violet plant was discovered by me in 1981 as a sport of the variety MELODIE Mary under culture at Hayward, Calif. With subsequent propagation of the new plant by means of leaf cuttings at Hayward, Calif., this sport has demonstrated that its distinctive characteristics hold true from generation to generation and appear to be firmly fixed.

DESCRIPTION OF THE PLANT

Sheet one is a full color photographic view of the plant in bloom, the colors shown being as nearly true as it is reasonably possible to obtain by conventional photographic procedures.

The following is a detailed description of my new African violet plant with the color designation being according to the R.H.S. Colour Chart published by The Royal Horticultural Society of London, England, with collaboration by The British Colour Council.

THE PLANT

Origin: Sport.
Parentage: MELODIE Mary.
Classification:
- *Botanic.*—*Saintpaulia ionantha.*
- *Commercial.*—African Violet.

Form: Compact potted plant.
Height: 9 To 11 cm. from base to top of flowers.
Growth: Condensed and vigorous with sturdy upright flower peduncles and fairly strong petioles which tend to spread horizontally.
Foliage: Abundant in quantity.
- *Size of Leaf.*—About 5.5 to 6 cm. long and about 4.5 to 5 cm. side.
- *Shape.*—Ovate to orbicular with crenate margins.
- *Texture.*—Upper side slightly hairy. Under side slightly hairy.
- *Color.*—Upperside, medium green. Underside, light green.
- *Petioles.*—Strong, medium green, medium hairy, length varies with age of leaf and plant.

THE FLOWER

Blooming habit: Continuous and abundant under optimum growing conditions.
Number: Three to six per peduncle.

Size of flower: Each flower is 3.2 to 4.2 cm. in diameter.
Shape of flower: Single to semi-double. Flat when mature.
Petalage: Five petals.
- *Arrangement.*—Sympetalous.
- *Form.*—Three larger and two smaller petals form a bilaterally symmetrical flower.
- *Texture.*—Smooth and flexible.
- *Appearance.*—Glitter on upper surface and shiny and bumpy on underside.
- *Color.*—Two smaller upper petals are Violet-Blue — 89C. The three lower larger petals are White — 155D towards the center of flower with Violet-Blue — 89C tips from R.H.S. Colour Chart.

Peduncle: Short, strong upright about 4.5 to 6.5 cm. Reddish to medium green.
Discoloration: Does not fade.
Persistence: The flowers hang on and dry.
Effect of weather: The plants thrive best in relatively high humidity.
Fragrance: None
Lasting quality: Ten to fourteen days for the fully opened flowers. Not recommended as cut flower.

REPRODUCTIVE ORGANS

Stamens: Usually 2 per flower and joined at top of anthers.
- *Anthers.*—Bright yellow, fade slightly as they get older, visible, one on each filament.
- *Filaments.*—Approximately 0.5 cm. long.
- *Pollen.*—Light yellow, ripens before stigma.

Pistils: Normally 1 per flower.
- *Style.*—Approximately 0.6 cm. long
- *Stigma.*—Usually visible and accessible; when receptive, it becomes swollen and usually exudes a small drop of clear liquid.

Ovaries: Superior.

This variety of African violet plant is very suited for potted plant culture and its year around blooming capability gives the plant a commercially attractive value. Older flowers do not fade. This new African violet is a good producer that is fairly disease resistant. The pansy-like blooms make this plant unique for an African violet.

I claim:

1. A new African violet plant, substanially as shown and described.

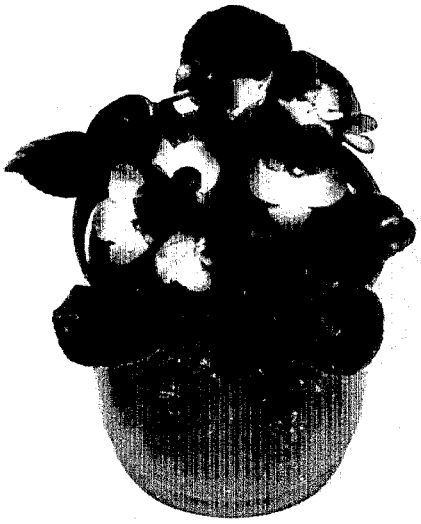

* * * * *